United States Patent [19]
Prasad et al.

[11] Patent Number: 6,127,566
[45] Date of Patent: Oct. 3, 2000

[54] PROCESS FOR THE SYNTHESIS OF O,O-DIMETHYL PHOSPHOROAMIDOTHIOATE

[75] Inventors: Vidyanatha A. Prasad, Leawood, Kans.; Donald K. Smith, Liberty, Mo.; David L. Meyer, Raytown, Mo.; Jonathan D. Spicher, Parkville, Mo.; Scott P. Hensley, Kansas City, Mo.

[73] Assignee: Bayer Corporation, Pittsburgh, Pa.

[21] Appl. No.: 09/153,913

[22] Filed: Sep. 16, 1998

[51] Int. Cl.$^7$ ........................................................ C07F 9/24
[52] U.S. Cl. ........................................... 558/138; 558/199
[58] Field of Search .............................................. 558/138

[56] References Cited

U.S. PATENT DOCUMENTS

| | | |
|---|---|---|
| 3,309,266 | 3/1967 | Magee . |
| 3,639,547 | 2/1972 | Magee . |
| 3,978,173 | 8/1976 | Kohn et al. .......................... 558/138 X |
| 4,001,353 | 1/1977 | Hofer .................................. 558/138 X |

FOREIGN PATENT DOCUMENTS

| | | | |
|---|---|---|---|
| 10-007691 | 1/1998 | Japan ................................ | C07F 9/24 |

OTHER PUBLICATIONS

Patent Abstracts of Japan, Japanese Patent Office, 1998, JP 10–007,691A.

*Primary Examiner*—Michael G. Ambrose
*Attorney, Agent, or Firm*—Joseph C. Gil; Carol Marmo

[57] ABSTRACT

The present invention provides a continuous process for making O,O-dimethyl phosphoroamidothioate. In accordance with this process, O,O-dimethyl phosphorochloridothioate is reacted with ammonia and sodium hydroxide; addition of the sodium hydroxide controls the pH of the reaction mixture. The formed reaction mixture contains an aqueous phase and an organic phase. The organic phase of the reaction mixture is separated from the aqueous phase; a second organic phase is solvent extracted from the aqueous phase; and the resultant O,O-dimethyl phosphoroamidothioate is isolated from the combined organic phases via vacuum solvent stripping. In an embodiment of the present invention, the reaction of O,O-dimethyl phosphorochloridothioate with ammonia and sodium hydroxide is carried out in the presence of a solvent.

19 Claims, No Drawings

PROCESS FOR THE SYNTHESIS OF O,O-DIMETHYL PHOSPHOROAMIDOTHIOATE

TECHNICAL FIELD OF THE INVENTION

The field of this invention is phosphoroamidothioate insecticides. More particularly, the present invention pertains to an improved continuous process for synthesizing O,O-dimethyl phosphoroamidothioate by controlling the pH of the reaction mixture with the addition of sodium hydroxide.

BACKGROUND OF THE INVENTION

O,O-dialkyl phosphoroamidothioates are intermediates used in the preparation of phosphoroamidothioate insecticides. In particular, O,O-dimethyl phosphoroamidothioate is an intermediate which is required in producing O,S-dimethyl phosphoroamidothioate. O,O-dimethyl phosphoroamidothioate is generally produced by reacting O,O-dimethyl phosphorochloridothioate with two equivalents of aqueous ammonia with or without a solvent. U.S. Pat. No. 3,309,266 discloses that O,O-dimethyl chlorophosphorothioate is reacted with ammonia or a primary alkylamine to produce O,O-dimethyl phosphoroamidothioate. In a manner similar to the method disclosed in U.S. Pat. No. 3,309,266, U.S. Pat. No. 3,639,547 discloses that O,O-dimethyl phosphoroamidothioate can be made via ammoniation of an O,O-dimethyl halophosphorothioate. With the above methods, the yield of the formed O,O-dimethyl phosphoroamidothioate is low, and the purification process, requiring ammonia recovery, is extensive. Thus, there continues to be a need in the art, for an efficient method for making O,O-dimethyl phosphoroamidothioate with an increased net yield, and preferably, without the need for an ammonia recovery procedure.

BRIEF SUMMARY OF THE INVENTION

The present invention provides a method for increasing the net yield of O,O-dimethyl phosphoroamidothioate. In accordance with the continuous process of the invention, O,O-dimethyl phosphorochloridothioate is reacted with ammonia and sodium hydroxide; the addition of sodium hydroxide controls the pH of the reaction mixture; the formed reaction mixture contains an aqueous phase and an organic phase; the organic phase of the reaction mixture is separated from the aqueous phase; a second organic phase is then solvent extracted from the aqueous phase; and the resultant O,O-dimethyl phosphoroamidothioate is isolated from the organic phases. In an embodiment of the present invention, O,O-dimethyl phosphorochloridothioate is reacted with ammonia and sodium hydroxide in the presence of a solvent. A preferred solvent of the invention is toluene.

It is an object of this invention to provide an improved process for synthesizing O,O-dimethyl phosphoroamidothioate. It is a further object of this invention to control the pH of the reaction mixture by the addition of sodium hydroxide, to produce optimum net yields of O,O-dimethyl phosphoroamidothioate.

DETAILED DESCRIPTION OF THE INVENTION

The present invention provides a method for increasing the net yield of O,O-dimethyl phosphoroamidothioate. The method of the present invention is a "split-alkali" continuous process. O,O-Dimethyl phosphorochloridothioate is reacted with ammonia and sodium hydroxide. The addition of sodium hydroxide is used to control the pH of the reaction mixture. The molar ratio of ammonia to O,O-dimethyl phosphorochloridothioate is from about 1.3:1 to about 1.6:1; and preferably from about 1.40:1 to about 1.45:1, and more preferably, about 1.41:1. The molar ratio of sodium hydroxide to O,O-dimethyl phosphorochloridothioate is from about 0.90:1 to about 1:1, and preferably from about 0.93:1 to about 0.96:1, and more preferably about 0.93:1. The pH of the reaction is from about 9.2 to about 10.2, and preferably from about 9.2 to about 9.3. The temperature of the reaction is from about 35° C. to about 45° C., and preferably 40° C. The residence time of the reaction is from about 2 hours to about 4 hours, and preferably about 3 hours.

In an embodiment of the present invention, the reaction of O,O-dimethyl phosphorochloridothioate with ammonia and sodium hydroxide is carried out in the presence of a solvent. An aromatic, aprotic solvent is preferred. Such solvents are well known in the art and include toluene, xylene, and mesitylene. Toluene is a preferred aromatic, aprotic solvent. The molar ratio of toluene to O,O-dimethyl phosphorochloridothioate is from about 0.5:1 to about 2:1, and preferably from about 0.75:1 to about 1:1.

The resulting reaction mixture contains an aqueous phase and an organic phase. The organic phase is separated from the aqueous phase in a batch separator. A second organic phase is then extracted from the aqueous phase of the reaction mixture. Vacuum solvent stripping is performed on the combined organic phases to produce the resultant O,O-dimethyl phosphoroamidothioate.

In a preferred embodiment of the present invention, a solvent is used to extract the second organic phase from the aqueous phase. The solvent may include any aromatic, aprotic solvent known in the art. Such solvents are the same as those solvents identified previously for use in the first reaction step. A preferred solvent is toluene.

The Examples that follow illustrate preferred embodiments of the present invention and are not limiting of the specification and claims in any way.

EXAMPLES

Example 1

Preparation of O,O-Dimethyl Phosphoroamidothioate Using a Neat (No Solvent) "Split Alkali" Continuous Process O,O-Dimethyl phosphorochloridothioate was charged to the reactor. Simultaneously, 25% sodium hydroxide was charged at a rate to maintain 0.93 molar equivalents with respect to O,O-dimethyl phosphorochloridothioate, and 18% ammonium hydroxide was charged at a rate to maintain 1.41 molar equivalents with respect to O,O-dimethyl phosphorochloridothioate. The reactants were added using variable speed peristaltic pumps. The flow rates were checked at regular intervals by weighing, and pump speeds were adjusted to maintain proper flow rates throughout the experiments. The residence time of the reaction was 3 hours. The reaction temperature was maintained at 40° C. with stirring. The reaction mixture was continuously removed to maintain the desired volume. The organic and aqueous phases were separated and the aqueous phase was solvent extracted to recover O,O-dimethyl phosphoroamidothioate. A net yield of about 98.5% O,O-dimethyl phosphoroamidothioate was realized.

Table 1 shows the % net yield of O,O-dimethyl phosphoroamidothioate produced by varying the pH of the reaction mixture. The pH was controlled by varying the molar ratio of sodium hydroxide to O,O-dimethyl phosphorochloridothioate. The molar ratio of ammonia to O,O-dimethyl phosphorochloridothioate was maintained at 1.41 and the temperature was maintained at 40° C. Optimum yields (98%–99%) were realized at a pH of 9.2–9.3, using a molar ratio of 0.93 mole of sodium hydroxide to 1 mole of O,O-dimethyl phosphorochloridothioate. Using a molar ratio of sodium hydroxide to O,O-dimethyl phosphorochloridothioate of 0.90 mole, resulted in the pH dropping to below 7; unreacted O,O-dimethyl phosphorochloridothioate occurred in the organic phase and the net yield decreased to 94.2%.

TABLE 1

| Moles NaOH per mol DMPCT* | % Net Yield | pH | % DMPCT* Org. Phase | % DMPCT* Aq. Phase |
|---|---|---|---|---|
| 0.93 | 98.5 | 9.2–9.3 | zero | 0.6 |
| 0.96 | 97.5 | 9.4–9.6 | zero | 1.6 |
| 0.90 | 94.2 | <7 | up to 3% | 2.2 |
| 0.95 | 98.1 | 9.3–9.5 | zero | 1.1 |
| 1.05 | 93.5 | 9.7–11.0 | zero | 4.8 |
| 1.00 | 93.8 | 9.8–10.2 | zero | 5.1 |

*DMPCT = Unreacted O,O-dimethyl phosphorochloridothioate

Table 2 shows the % net yield of O,O-dimethyl phosphoroamidothioate produced using the neat (i.e., no solvent) "split-alkali" process with varying temperatures, using 1.41 moles of ammonia, 0.93 moles of sodium hydroxide, and 1.0 mole of O,O-dimethyl phosphorochloridothioate. Optimum yield (98.5%) was realized at a temperature of 40° C. The yields at 35° C. and 45° C. were lower (94.2% and 95.9%, respectively).

TABLE 2

| Temp ° C. | % Net Yield | pH | % DMPCT* Org. Phase | % DMPCT* Aq. Phase |
|---|---|---|---|---|
| 40 | 98.5 | 9.2–9.3 | zero | 0.6 |
| 45 | 95.9 | 8.8–8.9 | zero | 4.4 |
| 35 | 94.2 | 8.8–9.1 | zero | 1.1 |

*DMPCT = Unreacted O,O-dimethyl phosphorochloridothioate

The process of the above-described test was repeated, except that a solvent was used. Thus, the reaction was conducted in toluene. The toluene was present in an amount such that the ratio of toluene to O,O-dimethyl phosphoroamidothioate was about 1:1. The results of this second test were similar to the results shown in Tables 1 and 2, above.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing O,O-dimethyl phosphoroamidothioate comprising:
   a. reacting O,O-dimethyl phosphorochloridothioate with ammonia and sodium hydroxide;
   b. forming a reaction mixture containing an aqueous phase and an organic phase, wherein pH of the reaction mixture is controlled by addition of the sodium hydroxide;
   c. separating the organic phase of the reaction mixture from the aqueous phase;
   d. extracting with a solvent a second organic phase from the aqueous phase; and
   e. isolating O,O-dimethyl phosphoroamidothioate from the organic phases.

2. The process of claim 1 wherein the molar ratio of ammonia to O,O-dimethyl phosphorochloridothioate is from about 1.3:1 to about 1.6:1.

3. The process of claim 1 wherein the molar ratio of ammonia to O,O-dimethyl phosphorochloridothioate is from about 1.4:1 to about 1.45:1.

4. The process of claim 1 wherein the molar ratio of ammonia to O,O-dimethyl phosphorochloridothioate is about 1.41:1.

5. The process of claim 1 wherein the molar ratio of sodium hydroxide to O,O-dimethyl phosphorochloridothioate is from about 0.90:1 to about 1:1.

6. The process of claim 1 wherein the molar ratio of sodium hydroxide to O,O-dimethyl phosphorochloridothioate is from about 0.93:1 to about 0.96:1.

7. The process of claim 1 wherein the molar ratio of sodium hydroxide to O,O-dimethyl phosphorochloridothioate is about 0.93:1.

8. The process of claim 1 wherein the pH is from about 9.2 to about 10.2.

9. The process of claim 1 wherein the pH is from about 9.2 to about 9.3.

10. The process of claim 1 wherein the temperature is from about 35° C. to about 45° C.

11. The process of claim 1 wherein the temperature is 40° C.

12. The process of claim 1 wherein the reaction in step a. is carried out in the presence of an aprotic, aromatic solvent.

13. The process of claim 12 wherein the solvent is one selected from the group consisting of toluene, xylene, and mesitylene.

14. The process of claim 12 wherein the solvent is toluene.

15. The process of claim 12 wherein the molar ratio of the solvent to O,O-dimethyl phosphorochloridothioate is from about 0.5:1 to about 2:1.

16. The process of claim 12 wherein the molar ratio of the solvent to the O,O-dimethyl phosphorochloridothioate is from about 0.75:1 to about 1:1.

17. The process of claim 1 wherein the second organic phase in step d. is extracted using an aprotic, aromatic solvent.

18. The process of claim 17 wherein the solvent is toluene.

19. The process of claim 1 wherein the O,O-dimethyl phosphoroamidothioate is isolated from the organic phase via vacuum solvent stripping.

* * * * *